United States Patent [19]

Walters

[11] Patent Number: 4,731,484

[45] Date of Patent: Mar. 15, 1988

[54] HALOACETYL DERIVATIVES OF AROMATIC COMPOUNDS

[75] Inventor: Marlin E. Walters, West Columbia, Tex.

[73] Assignee: The Dow Chemical Company, Midland, Mich.

[21] Appl. No.: 858,133

[22] Filed: Apr. 30, 1986

Related U.S. Application Data

[63] Continuation-in-part of Ser. No. 692,462, Jan. 18, 1985, abandoned.

[51] Int. Cl.[4] ............................................ C07C 49/213
[52] U.S. Cl. .................................... 568/331; 568/325; 568/327; 568/328; 568/43; 568/42; 568/17; 564/433
[58] Field of Search ............... 568/327, 328, 325, 331, 568/43, 42, 17; 504/433

[56] References Cited

U.S. PATENT DOCUMENTS

| | | | |
|---|---|---|---|
| 3,150,187 | 9/1964 | Cavallini et al. | 568/331 |
| 3,450,770 | 6/1969 | Bridger et al. | 568/331 |
| 3,580,927 | 5/1971 | Wear | 568/325 |
| 3,624,142 | 11/1971 | Shen et al. | 568/331 |
| 3,706,803 | 12/1972 | Sella et al. | 568/325 |
| 4,202,960 | 5/1980 | Robilloud et al. | 568/331 |

FOREIGN PATENT DOCUMENTS 1028108  5/1966  United Kingdom ............... 568/331

*Primary Examiner*—James H. Reamer
*Attorney, Agent, or Firm*—A. Cooper Ancona

[57] ABSTRACT

New compounds which are 4,4'-bis(trihaloacetyl) derivatives of aromatic compounds have been prepared by reacting an aromatic compound with a haloacetyl halide in the presence of a Friedel-Crafts catalyst, e.g. AlCl$_3$, in a suitable solvent. The compounds are useful in preparing polycarbonates, polyesters, polyamides, polyketones and polyurethanes.

20 Claims, No Drawings

HALOACETYL DERIVATIVES OF AROMATIC COMPOUNDS

CROSS REFERENCE TO RELATED APPLICATION:

This application is a continuation-in-part of copending application of Ser. No. 692,462, filed Jan. 18, 1985 now abandoned.

BACKGROUND OF THE INVENTION

Trichloromethylketones have been known for nearly 100 years. Gautier (Ann. chim., (6) 14, 345 [1888]) first prepared 2′,2′,2′-trichloroacetophenone by acylation of benzene with trichloroacetylchloride in 1888. Although there have been attempts to improve the results of this reaction (Blitz, H., J. Prakt. Chem., (2) 142 193 [1935]; Kaluszyner, A. and Reuter, S., J. Am. Chem. Soc., 75, 5126 [1953]) they have met with little success. Alternative methods for preparing trichloromethylketones have been reported which have the advantage of improved yields such as Houben's (Ber., 59B, 2878 [1926]) nitrile reaction and more recently the oxidation of the corresponding secondary alcohols (Shono, T., Kise, N., Yamazaki, A., and Ohmizu, H., Tetrahedron Lett., 23, 1609 [1982]; Atkins, P. J., Gold, V., and Wassef, W. N., J. Chem. Soc., Chem. Commun., 283 [1983]). Although the latter methods show some improvement, the yields, in general, are less than 50%.

The present invention employs a much improved method for the preparation of trihalomethyl ketones from trihaloacetylchloride and an aromatic compound. This invention relates to novel trihaloacetyl compounds and more particularly to aryl bis(trihaloacetyl) derivatives having the formula:

$$X_3C-\overset{O}{\underset{\|}{C}}-B_1-A-B_2-\overset{O}{\underset{\|}{C}}-CX_3$$

wherein $B_1$ and $B_2$ are independently selected from

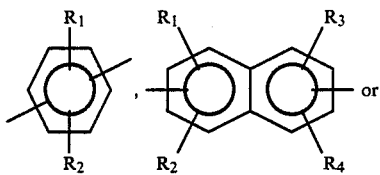
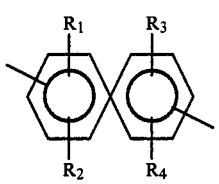

and which may be the same or different and wherein $R_1$, $R_2$, $R_3$ and $R_4$ are independently selected from the group consisting of hydrogen, chlorine, bromine, an alkyl or an alkoxy group having from 1 to 4 carbon atoms, a phenyl group or

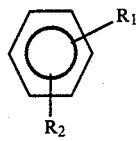

wherein $R_1$ and $R_2$ have the aforesaid meaning, X is chlorine or bromine and A is a single valence bond, oxygen, sulfur,

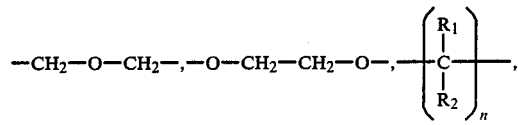

an aromatic group having the formula

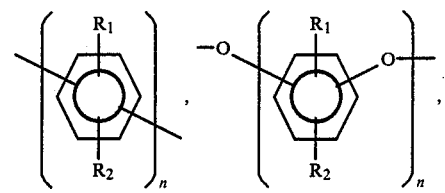

X, $R_1$, $R_2$, $R_3$ and $R_4$ having the aforesaid meanings and wherein n is an integer from 1 to 6.

Although U.S. Pat. No. 3,150,187 claims aryl dihalogenacetyl derivatives as useful materials which inhibit the growth of *Mycobacterium tuberculosis* no mention is made of the trihalogenacetyl derivatives or of any use of them.

The present invention involves the reaction of an aromatic compound with a haloacetyl halide in the presence of a Friedel-Crafts catalyst.

SUMMARY OF THE INVENTION

New compounds which are 4,4'-bis(trihaloacetyl) derivatives of aromatic compounds have been prepared by reacting an aromatic compound with a haloacetyl halide in the presence of a Friedel-Crafts catalyst, e.g. AlCl₃, in a suitable solvent. The compounds are useful in preparing polyesters, polyamides and polyketones by reacting with dihydric alcohols, diamines and diacetyl compounds, respectively.

DETAILED DESCRIPTION OF THE INVENTION

The compounds of the present invention are prepared by reacting an aromatic compound with trichloroacetylchloride, tribromoacetylbromide and the like trihaloacetyl halides in a solvent and in the presence of a Friedel-Crafts catalyst. The reaction is preferably conducted at a temperature of from about 20° to about 45° C. but may be run at higher temperatures of up to about 85° C. Temperatures above the boiling point of the solvent employed require the use of pressure.

Solvents useful in the process of the invention are solvents having boiling points of from about 20° to about 135° C. and include methylene chloride, perchloroethylene, dichloroethanes, carbon tetrachloride, carbon disulfide, trichloroacetylchloride, halobenzenes, nitroalkanes and other saturated hydrocarbons and their halogenated derivatives having appropriate boiling points providing there is no adverse reaction with the catalyst which might deplete or destroy it.

Useful catalysts for the reaction include FeCl₃, AlCl₃, TiCl₄, ZrCl₄, HfCl₄, TaF₅ and combinations thereof. Aluminum chloride is the preferred catalyst.

The amount of catalyst employed is from about 0.5 to about 4 mols per mol of aromatic compound, but preferably is about 2 to 3. More than about 3 mols of catalyst per mol of aromatic compound is of no advantage.

Pressure normally employed is at or near atmospheric, but if necessary to prevent evaporation of the solvent pressures up to 10 atmospheres may be employed. Atmospheric pressure, however, is preferred.

Mole ratios of reactants employed can be from about 2 to about 12 mols of trichloroacetylchloride per mol of aromatic compound. The preferred ratio is from about 2/1 to about 4/1.

The time of reaction is dependent on the temperature and catalyst employed, but is generally from about 0.5 to about 24 hours and preferably from about 2 to about 6 hours.

Representative compounds suitable for acylation with trichloroacetylchloride are biphenyl, phenyl ether, diphenylmethane, diphenylethane, diphenylpropane, diphenylbutane, diphenylethylene, diphenyldichloromethane, 1,1,1-trichloro-2,2-bis(phenyl)ethane, 1,1-dichloro-2,2-bis(phenyl)ethane, 1-chloro-2,2-bis(phenyl)ethane, terphenyl, diphenyl sulfide, diphenylamine, diphenylbenzidine, diphenylmethoxyphosphine, diphenylethoxyphosphine, triphenylphosphine, diphenylfulvene, diphenylphosphine, diphenylmethylsilane, diphenyldimethylsilane, diphenylsilane, diphenoxybenzene, phenoxybiphenyl, 1,4-bis-(4-phenyl phenoxy)benzene, 4,4'-bis(4-phenylphenoxy)biphenyl, 1,4-bis-(4-phenylphenoxy)naphthalene, 1,5-bis-(4-phenylphenoxy)naphthalene, diphenoxynaphthalene, naphthyl ether, dinaphoxybenzene, dinaphthoxynaphthylene, diphenoxyethane, benzyl ether and 4,4'-diphenoxybiphenyl.

The reaction to make these products is illustrated in the following example.

EXAMPLE 1

A slurry of AlCl₃ (2.2 mols, 293.26 g) in CH₂Cl₂ (200 ml) was prepared in a flask and trichloroacetylchloride (2.0 mols, 363.66 g, TCAC) was added to the mixture from a dropping funnel. Diphenyl ether (1.0 mol, 170.21 g DPE) was added dropwise over a two-hour period with vigorous stirring. The temperature of the mixture rose from 23° C. to 32° C. and remained there throughout the reaction. The reaction mixture was poured over ice and the aqueous and organic phases were separated. The CH₂Cl₂ solution was washed with saturated aqueous NaHCO₃ (2×500 ml) then dried over MgSO₄, filtered and the solvent was removed by evaporation at reduced pressure, leaving the desired 4,4'-bis-(trichloroacetyl)phenyl ether, which has the following structure:

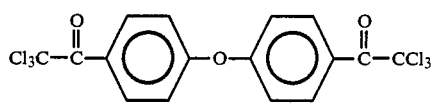

The white crystals had a melting point of 129°–130° C. The yield of crystals was 194.8 g or 42.3% of theoretical.

A purer product can be obtained by dissolving the crystals in methylene chloride and then extracting impurities, mainly color bodies, by contacting with concentrated H₂SO₄.

The following example illustrates the use of 1,2-dichloroethane (EDC) as the solvent.

EXAMPLE 2

A slurry of AlCl₃ (7.50 mols, 1000 g) was prepared in EDC (1500 ml) and the trichloroacetylchloride (TCAC) (5.00 mols, 909.15 g) was added to the mixture in one portion. The mixture was brought to 40° C. and the diphenyl either (2.50 mols, 425.5 g, 396.6 ml), dissolved in EDC (100 ml), added dropwise with vigorous stirring over a 2 hour period. The temperature rose to 48° C. and stabilized during the addition. The reaction mixture was poured over ice (3000 g) and extracted with EDC (1000 ml) from which crystals of the product, 4,4'-bis(trichloroacetyl)phenyl ether, were collected upon concentration and cooling of the solution. 943.82g or 82% of theory, m.p. 129°–130° C.

In the following example excess reactant TCAC is used as the solvent.

EXAMPLE 3

A slurry of AlCl₃ (0.44 mols, 59.0 g) was made in TCAC (1.46 mols, 265.75 g, 200 ml) and the mixture brought to 30° C. Diphenyl ether (0.20 mol, 34.04 g) dissolved in TCAC (0.44 mol, 80.0 g, 60 ml) was added over a 35 minute period during which time the reaction temperature rose to 40° C. The mixture was stirred for 6 hours and then worked up as in the previous example yielding 82.92 g (89.9%) of 4,4'-bis(trichloroacetyl)phenyl ether.

Perchloroethylene was also used effectively as a solvent, but gave a somewhat lower yield (ca. 80–85%) under substantially the same reaction conditions.

The following example illustrates the use of a mixed solvent system for the reaction.

EXAMPLE 4

This reaction was run exactly as that described in Example 3 except that a mixture composed of 80% TCAC and 20% perchloroethylene by weight was used as the solvent. Thus, 0.44 mol AlCl₃ was slurried in 200 ml of the solvent mixture to which 0.20 mol of diphenyl ether in 60 ml of the solvent mixture was added in 25 minutes. The reaction was worked up after 6 hours as in the above examples yielding 83.61 g (90.7%) of 4,4'-bis(-trichloroacetyl)phenyl ether.

The following example illustrates an improved method for the purification of the crude products obtained in these reactions.

EXAMPLE 5

The crude product obtained from several batches from the reaction of trichloroacetylchloride and phenyl ether conducted as in one or more of Examples 1–3 above (2613.0 g) was charged into a 12 liter flask equipped with a mechanical stirrer, nitrogen supply and a thermometer. Methylene chloride (8.0 liters) was added followed by sulfuric acid (98%, 1.0 liter) and the mixture stirred at 35° C. for 24 hours. The mixture was transferred to a separatory funnel and the organic solution separated from the sulfuric acid. The organic layer was than filtered through a short column of silica gel (to remove residual H₂SO₄) and the solvent removed by evaporation leaving 2556.07 g (97.82%) of snow white crystals which had a very sharp melting point at 130° C.

Examples of reacting other aromatic compounds with trichloroacetylchloride are shown in Examples 6–11 below.

EXAMPLE 6

A slurry of AlCl₃ (20 g, 0.15 mol) was made in trichloroacetylchloride (81.5 g, 0.45 mol, 50 ml) under argon at 40° C. for 45 min. A solution of 1,4-diphenoxybenzene (10.48 g, 0.04 mol) in perchloroethylene (25 ml) was added dropwise over 15 minutes. The brown mixture was stirred at 40° C. for 2 hours and poured over ice (300 ml) and stirred for 1 hour. The colorless precipitate was filtered and dried (22 g, 99.5%) and recrystallized from perchloroethylene to give the desired 1,4-bis(p-trichloroacetyl-phenoxy) benzene as colorless crystals. The crystals had a melting point of 215°–217° C. and have the structure

A slightly different preparation of the above compound was made as shown in the following example.

EXAMPLE 7

1,4-Bis-(4'-trichloroacetylphenoxy)benzene

To a stirred solution of 1,4-diphenoxybenzene (15.72 g, 0.06 mol) in trichloroacetylchloride (50 ml, 30.69 g, .168 mol) under argon was added AlCl₃ (18.5 g, 0.139 mol) all at once. The mixture was stirred and heated at 40° C. over 1 hour. After cooling the mixture was poured into 500 g of crushed ice. The resulting colorless crystalline solid was filtered and washed with water. After suction drying overnight the crystals weighed 33 g (99.5% of theory) and had an m.p. of 215°–217° C.

EXAMPLE 8

BIS-(TRICHLOROACETYL)BIPHENYL

The AlCl₃ (80.0 g, 0.60 mol) was weighed into a 500 ml flask which had been flushed with nitrogen. The AlCl₃ was then covered with 50 ml of methylene chloride and the TCAC (90.9 g, 0.50 mol) added with stirring. The reaction mixture was brought to 30° C. and the biphenyl (38.55 g, 0.25 mol) dissolved in CH₂Cl₂ (50 ml) was added dropwise over 1 hour. After the mixture had cooled to 25° C. the mixture was poured over ice and extracted with CH₂Cl₂ (300 ml). The organic layer was washed with water, dried over MgSO₄, filtered and concentrated leaving 60.7 g of pale yellow crystals. m.p. 137° C.–152° C. GC. Mass Spec. analysis shows the product to be a mixture of the 2,4- and 4,4'-isomers, 80% of which was the 4,4'- product.

EXAMPLE 9

BIS-(TRICHLOROACETYL)PHENOXYBIPHENYL

A mixture of TCAC (25 ml), AlCl₃ (10.66 g, 0.08 mol) and CH₂Cl₂ (40 ml) was stirred at 20° C. under argon for 15 minutes. A solution of 4-phenoxybiphenyl (4.92 g, 0.02 mol) in CH₂Cl₂ (30 ml) was added dropwise over 15 minutes and the dark mixture was stirred at 20° C. for 4 hours. The usual workup gave a semisolid product which failed to crystallize. GC. Mass Spec. analysis showed this product to be a mixture of isomers of bis-(trichloroacetyl)phenoxybiphenyl, 80% of which was 4-(trichloroacetyl)phenoxy-4'-(trichloroacetyl)biphenyl.

EXAMPLE 10

4,4'-BIS(TRICHLOROACETYL)-3-METHYLDIPHENYL ETHER

The AlCl₃ (200 g, 1.50 mol) was weighed into a 500 ml round bottom flask equipped with mechanical stirrer, thermocouple and a dropping funnel. TCAC (250 ml) was added and the resulting gray suspension stirred for one hour at 23° C. The phenyltolyl ether (92.1 g, 0.050 mol) was then added dropwise from the addition funnel as a solution in 30 ml TCAC over a 60-minute period. The temperature rose to 43° C. as the mixture darkened. The mixture was stirred at 45° C. for an additional 60 minutes and then poured over ice and extracted with CH₂Cl₂. After drying and concentration crystals of 4,4'-bis(trichloroacetyl)-3-methyldiphenyl ether were collected (223.2 g, 94%) m.p. 120°–124° C.

EXAMPLE 11

4,4'-BIS(TRICHLOROACETYL)DIPHENYLMETHANE

The AlCl₃ (200 g, 1.50 mol) was weighed into a 500 ml round bottom flask equipped with mechanical stirrer, thermocouple and a dropping funnel. TCAC (250 ml) was added and the resulting gray suspension stirred for 1 hour at 24° C. The diphenylmethane (84.12 g, 0.50 mol) was then added from the dropping funnel dropwise as a solution in 30 ml TCAC over a 45 minute period. The temperature rose from 24° C. to 45° C. as the diphenylmethane was added. The mixture was stirred at 45° C. for an additional 60 minutes and then worked up as usual. The product crystallized from petroleum ether had an m.p. of 123°–125° C.

The bis(trichloroacetyl) compounds, as exemplified above, are useful in making polymers. Representative such compounds are: 4,4'-bis(trichloroacetyl) ether, 1,4-bis(trichloroacetylphenoxy)benzene, bis(trichloroacetyl)biphenyl, bis(trichloroacetyl)phenoxybiphenyl, 4,4'-bis(trichloroacetyl)3-methyldiphenyl ether, 4,4'-bis(trichloroacetyl)diphenylmethane, 1,1-bis[4-[4-(trichloroacetyl)phenoxy]phenyl)-2,2,2-trichloroethane, 4,4'-bis(4-(trichloroacetyl)phenoxy]-diphenylmethane.

The difunctional compounds which are reacted with the above bis(trichloroacetyl) compounds are enumerated in the following paragraphs.

Representative of the dihydric alcohols for the polyester reaction are bisphenol A (p,p'-isopropylidene diphenol), resorcinol, hydroquinone, [1,1'-biphenyl]-4,4'-diol, 1,5-dihydroxynaphthalene, 1,1-dichloro-2,2-bis-(4-hydroxyphenyl)ethylene, 1-(4-hydroxyphenyl)-1,3,3-trimethyl-7-hydroxyindane, 4,4'-dihydroxyphenyl ether, 1,4-dihydroxy anthraquinone, 3,3',5,5'-tetramethyl-4,4'-dihydroxybiphenyl, 1,4-cyclohexanediol; also alkylene glycols, e.g. ethylene and propylene glycols, 1,4-butanediol and polyols.

Representative of the diamines used to form the polyamides are ethylene diamine, 1,6-diaminohexane, propylene diamine, 4,4'-diaminobiphenyl, p-phenylenediamine, m-phenylenediamine, 2,4-diaminotoluene, 1,5-diaminonaphthalene, 4,4'-methylenedianiline, diaminodiphenylsulfone, 4,4'-diaminodiphenylamine, 4,4'-diaminophenyl ether, 1,6-hexanediamine, 1,4-butanediamine, piperazine, aminoethylpiperazine, 1,4-cyclohexanediamine, 4,4'-trimethylenedipiperidine and bis(amino)polyglycols.

Representative diacyl aromatic compounds used to form the polyketones are the diacetylbenzenes (o-, m- or p-), 4,4'-bis(acetyl)phenyl ether, 1,4-bis(acetylphenoxy)benzene, bis(acetylphenoxy)biphenyl, 4,4'-diacetylbiphenyl, 2,3-butanedione, 4,4'-bis(acetyl)diphenylmethane, 4,4'-bis(acetyl)diphenyl-2,2-propane and 4,4'-bis(acetyl)3-methyldiphenyl ether.

The reaction to make the polyesters, polyamides and polyketones is generally conducted in the presence of a basic catalyst. If, however, the reactant amine is sufficiently basic, no catalyst is required.

While the reaction can be conducted in a melt of the reactants, a polar aprotic solvent is frequently used to advantage. Representative of such solvents useful in the reaction include tetrahydrofuran (THF), sulfolane, ρ-butyrolactone, dimethylsulfoxide (DMSO), dimethylacetamide, dimethylformamide (DMF), and N-methylpyrrolidone.

The catalysts useful in the reaction are basic catalysts. Alkali metal hydrides, e.g. NaH, can be employed and also tertiary amines, such as trialkyl amines, e.g. triethyl amine. Other tertiary amines which are useful catalysts include 1,4-diazobicyclo[2.2.2]-octane, 1,5-diazobicyclo[4.3.0]non-5-ene and dimethylaminopyridine. Lithium alkyls and amides, e.g. butyl lithium and diisopropyl lithium amide, are also good catalysts for the reaction.

The reaction may be conducted over a broad temperature range from about $-100°$ C. to about $+200°$ C., preferably from about $-45°$ C. to about $+85°$ C. One of the advantages of this process is the low temperature at which it may be conducted, which avoids decomposition which can occur at higher temperatures.

Another advantage is the time needed for the reaction to take place which will vary with the temperature, the reactivity of the alcohols, the particular trichloromethylketones employed and the catalyst used, if any, but it is generally accomplished in from about 1 minute to 24 hours and preferably from about 6 minutes to about 12 hours. The reaction is normally very rapid at room temperatures and requires less than an hour, usually only a few minutes.

Temperatures and times outside these ranges generally result in little or no reaction or poor yields due to incomplete reaction or decomposition of the products.

Pressures may be employed within the range of from about 20 to 760 mm Hg. Higher pressure can be employed, but is of no particular advantage. The pressure employed is not a critical variable.

The following examples are representative of the polymerization reactions for making polyesters, polyamides and polyketones from the compounds of the invention.

EXAMPLE 12

A Polyester from 4,4'-Bis(tricholoacetyl) phenyl ether and ethylene glycol

This polymerization was performed by weighing the reactants 4,4'-bis(trichloroacetyl)phenyl ether (0.20 mol, 92.19 g), ethylene glycol (0.20 mol, 12.41 g) and solvent (THF, 200 ml) into a 500 ml resin flask, bringing the mixture to 55° C. and adding the catalyst (NaH, 0.006 mol, 0.144 g). After stirring overnight the mixture was poured into acidic methanol and the polymer collected by filtration as a fine white powder, 55.76 g. DSC showed the polymer to have a glass transition temperature (Tg) of 116.7° C. and a crystalline melt temperature (Tm) of 158.8° C.

EXAMPLE 13

A POLYAMIDE FROM 4,4'-BIS(TRICHLOROACETYL)-PHENYL ETHER AND PIPERAZINE

The 4,4'-bis(trichloroacetyl)phenyl ether 0.20 mol, 92.19 g) was weighed into a resin flask equipped with a mechanical stirrer, thermowell, condenser and $N_2$ source. Dimethylacetamide (DMA) (150 ml) was added and the mixture brought to 60° C. to dissolve the ketone. The piperazine 0.20 mol, 17.23 g) was added in one portion with vigorous stirring. The temperature of the mixture rose at once and finally reached 105° C. after 6 minutes. The reaction mixture was allowed to cool, then poured into water (400 ml) and the polymer collected as a pale yellow powder 63.5 g (100%). The polymer was compression molded at 220° C. and 5000 lb/in². Differential scanning calorimetry (DSC) shows the Tg to be 202° C.

EXAMPLE 14

A POLYAMIDE FROM 4,4'-BIS(TRICHLOROACETYL)PHENYL ETHER AND AMINOETHYLPIPERAZINE

This polymerization was performed as in the example above by weighing the 4,4'-bis(trichloroacetyl)-phenyl ether 20 mol, 92.19 g) and DMA (150 ml) into a 500 ml resin flask, bringing the mixture to 60° C. and adding the aminoethylpiperazine 0.20 mol, 25.84 g). The polymer reaction mixture was allowed to cool, then poured into water (400 ml) and the polymer isolated as a gum which after drying was compression molded into flexible, ductile bars. DSC shows Tg to be 187°C. Thermal gravimetric analysis (TGA) shows the polyamide to be thermally stable having only 5% weight loss at 310° C.

EXAMPLE 15

A POLY-β-DIKETONE FROM 4,4′-BIS(TRICHLORACETYL)PHENYL ETHER AND 4,4′-BIS (ACETYL)-PHENYL ETHER

In a 250 ml flask under $N_2$ diisopropylamine 0.044 mol, 4.45 g) was dissolved in 100 ml THF and the solution cooled to $-70°$ C. in a Dry Ice/acetone bath. n-Butyllithium 0.044 mol, 2.81 g, 1.6M in hexane) was added via syringe while holding the temperature of the mixture below $-50°$ C. 4,4′-bis(acetyl)phenyl ether 0.020 mole, 5.09 g) in 20 ml THF was added dropwise to this mixture with stirring while allowing the temperature to rise to $-30°$ C. After stirring at $-30°$ C. for 30 minutes 4,4′-bis(trichloroacetyl)phenyl ether (0.020 mol, 9.22 g) in 20 ml THF was added via syringe. When the addition was complete the mixture was allowed to stir and warm to room temperature overnight, then poured into 500 ml of 0.01N HCl, the precipitate collected on a filter and washed with water (300 ml) and acetone (300 ml). The polymer was compression molded at 255° C./ 5000 psi and has a Tg=179° C. and Tm=323° C. by DSC.

In a similar manner a mixture of bis(acetyl)-phenyl ether and a bisphenol can be reacted with the bis(trichloroacety)aromatic compound to give a copolymer containing both ester and ketone groups in the polymer chain.

A more detailed description and other examples of the polymers which can be made from the bis(trichloroacetyl) compounds of the present invention can be found in a copending application of the inventor of this application, entitled "A New Method for Making Polyesters, Polyamides and Polyketones, Ser. No. 740,451, filed June 3, 1985.

I claim:

1. A compound having the formula:

wherein $B_1$ and $B_2$ are independently selected from

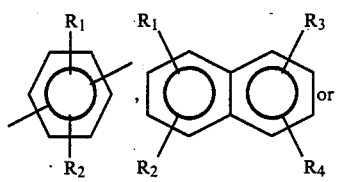

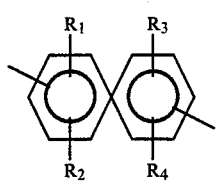

and which may be the same or different and wherein $R_1$, $R_2$, $R_3$ and $R_4$ are independently selected from the group consisting of hydrogen, chlorine, bromine, an alkyl or an alkoxy group having from 1 to 4 carbon atoms, a phenyl group or

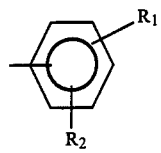

wherein $R_1$ and $R_2$ have the aforesaid meaning, X is chlorine or bromine and A is a single valence bond, oxygen, sulfur,

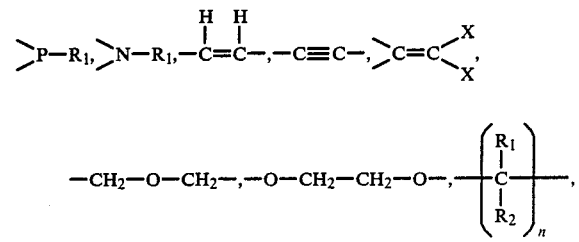

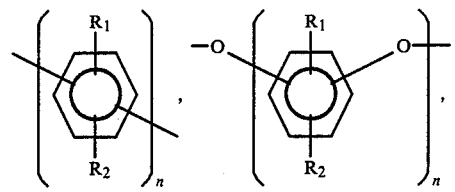

an aromatic group having the formula

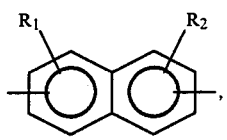

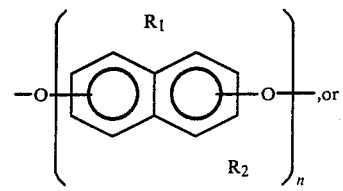

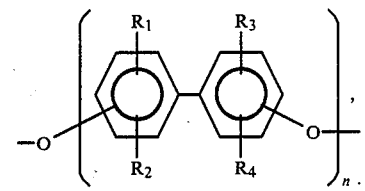

X, $R_1$, $R_2$, $R_3$ and $R_4$ having the aforesaid meanings and wherein n is an integer from 1 to 6.

2. The compound of claim 1 wherein A is oxygen.
3. The compound of claim 1 wherein A is a single valence bond.
4. The compound of claim 1 wherein A is sulfur.
5. The compound of claim 1 wherein A is

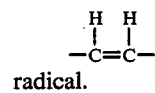

radical.

6. The compound of claim 1 wherein A is —C=C—.

7. The compound of claim 1 wherein A is >N—$R_1$.

8. The compound of claim 1 wherein A is >P—$R_1$.

9. The compound of claim 1 wherein A is a methylene group.

10. The compound of claim 2 wherein $B_1$ and $B_2$ are each

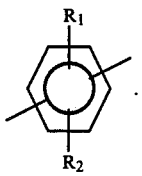

11. The compound of claim 10 wherein $R_1$ and $R_2$ are each hydrogen on each of $B_1$ and $B_2$.

12. The compound of claim 10 wherein at least one of the R groups is an alkyl radical and the remainder are hydrogen.

13. The compound of claim 12 wherein the alkyl radical is methyl.

14. The compound of claim 13 wherein $B_1$ is phenylene and $B_2$ is tolylene.

15. The compound of claim 2 wherein $B_1$ is

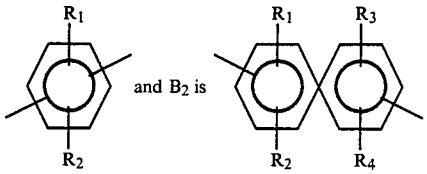

and $B_2$ is

16. The compound of claim 15 wherein $R_1$, $R_2$, $R_3$ and $R_4$ are each hydrogen.

17. The compound of claim 10 wherein A is

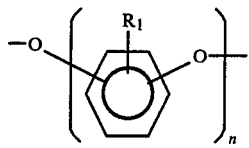

18. The compound of claim 17 wherein n is 1.

19. The compound of claim 3 wherein $B_1$ and $B_2$ are each

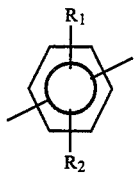

20. The compound of claim 19 wherein each of $R_1$ and $R_2$ in each of $B_1$ and $B_2$ are hydrogen.

* * * * *